United States Patent [19]

Volk et al.

[11] 4,415,750
[45] Nov. 15, 1983

[54] PROCESS FOR SEPARATION OF 2-HYDROXYNAPTHALENE-3-CARBOXYLIC ACID FROM THE REACTION MIXTURES OF ALKALI METAL SALTS OF 2-HYDROXYNAPHTHALENE AND CARBON DIOXIDE

[75] Inventors: Heinrich Volk, Bad Vilbel; Theodor Papenfahs, Frankfurt am Main, both of Fed. Rep. of Germany

[73] Assignee: Hoechst Aktiengesellschaft, Frankfurt am Main, Fed. Rep. of Germany

[21] Appl. No.: 358,314

[22] Filed: Mar. 15, 1982

Related U.S. Application Data

[63] Continuation of Ser. No. 264,826, May 18, 1981, abandoned, which is a continuation of Ser. No. 131,680, Mar. 19, 1980, abandoned.

[30] Foreign Application Priority Data

Mar. 24, 1979 [DE] Fed. Rep. of Germany ....... 2911667

[51] Int. Cl.$^3$ .............................................. C07C 51/43
[52] U.S. Cl. .................................................. 562/467
[58] Field of Search ......................................... 562/467

[56] References Cited

U.S. PATENT DOCUMENTS

| | | | |
|---|---|---|---|
| 2,723,290 | 11/1955 | Klein et al. | 562/467 |
| 3,468,942 | 9/1969 | Blum | 562/467 |
| 3,530,174 | 9/1970 | Gottisman et al. | 562/467 |
| 4,020,102 | 4/1977 | Seiger et al. | 562/467 |
| 4,057,576 | 11/1977 | Backmann et al. | 562/467 |

OTHER PUBLICATIONS

Gladilin et al., Chem. Abst., vol. 90, #121, 290m (1978).

*Primary Examiner*—James H. Reamer
*Attorney, Agent, or Firm*—Connolly and Hutz

[57] ABSTRACT

In the carboxylation of 2-alkali metal naphtholates under pressure and at temperatures of above 200° C., apart from the alkali metal salt of 2-naphthol-3-carboxylic acid and free 2-naphthol considerable amounts of resinous by-products are obtained which according to the hitherto known processes have to be separated and removed in a very expensive manner. According to this invention, the alkali-soluble acidic resins are separated from this carboxylation melt after its solution in water during the work-up of the carboxylation product by means of a cationic quaternary ammonium compound. These surface-active compounds precipitate the alkali-soluble acidic resins in such a manner that they can be easily removed from the alkali metal salts of 2-hydroxynaphthalene-3-carboxylic acid dissolved in water.

5 Claims, No Drawings

PROCESS FOR SEPARATION OF 2-HYDROXYNAPTHALENE-3-CARBOXYLIC ACID FROM THE REACTION MIXTURES OF ALKALI METAL SALTS OF 2-HYDROXYNAPHTHALENE AND CARBON DIOXIDE

This application is a continuation of application Ser. No. 264,826 filed May 18, 1981 and now abandoned, which in turn is a continuation of application Ser. No. 131,680 and now abandoned.

CROSS REFERENCE TO RELATED APPLICATION

The present invention relates to the field of intermediate product manufacture, especially to the manufacture of known starting products for water-insoluble azo dye-stuffs, namely 2-hydroxynaphthalene-3-carboxylic acid.

In the carboxylation of sodium salt of 2-hydroxynaphthalene under pressure and at temperatures of above 210° C., there are formed, in addition, to sodium salt of 2-hydroxynapthalene-3-carboxylic acid and free 2-hydroxynaphthalene, considerable amounts of resinous by-products which according to the known industrial processes must be separated in a very expensive manner from the intended naphthalenecarboxylic acid (see FIAT Final Report No. 1308). These high molecular weight impurities generally unknown with respect to their composition and constitution can be arranged in two groups of resins, that is, the alkali-insoluble and the alkali-soluble ones. The alkali-insoluble resins contain probable units having a xanthene or ketone structure, and the alkali-soluble resins can form salts more or less soluble in water due to their content of hydroxy and/or carboxy groups. While the alkali-insoluble resins can be separated easily from the hot, alkaline carboxylation reaction mixture diluted with water by usual equipment such as filters, separators, etc., and thus be separated from the aqueous-alkaline solution of 2-hydroxynaphthalene-3-carboxylic acid, removal of the water-soluble resins, especially their carboxy group-containing components of higher acidity, from the reaction mixture is technically insufficient hitherto.

For example, work-up of the carboxylation melt diluted with water is carried out in the industrial practice by neutralizing first to a pH of from about 6 to 8, thus converting sodium salt of 2-hydroxynaphthalene possibly still present to free 2-hydroxynaphthalene which dissolves in water at the preferred temperatures of from 80° to 95° C. On adjustment of the pH to about 6 to 8, those amounts of alkali-soluble resins which are only weakly acidic due to phenolic groups precipitate and can be removed in usual manner together with the alkali-insoluble resins separated already when mixing the carboxylation melt with water. From the remaining neutralized hot aqueous solution of monosodium salt of 2-hydroxynaphthalene-3-carboxylic acid and 2-hydroxynaphthalene, the dissolved 2-hydroxynaphthalene precipitates on cooling to 20°–30° C. and can be isolated subsequently from the aqueous solution of the product of the process for example by filtration. The high molecular weight resins of higher acidity still contained in the aqueous solution in the form of sodium salt could not be removed hitherto from the 2-hydroxynaphthalene-3-carboxylic acid, because they precipitated together with said naphthoic acid on isolation thereof by acidic precipitation at elevated temperature (80° to 95° C.). Thus, a final product contaminated by resin was the result, which fact causes problems on processing of this product, for example for the preparation of arylamides of 2-hydroxynaphthalene-3-carboxylic acid which are extremely important as coupling components in ice-color dyeing or as starting products for the colour pigment manufacture, and result in a considerably reduced quality.

It is therefore the object of this invention to provide a method for separating these high-acidity resins from the intended 2-hydroxynaphthalene-3-carboxylic acid, which, moreover, can be fitted without problems into the usual work-up of the carboxylation mixture to yield 2-hydroxynaphthalene-3-carboxylic acid, especially in order to avoid additional investment and labor coat as for as possible.

This object is achieved in accordance with the present invention by a process for the separation and isolation of 2-hydroxynaphthalene-3-carboxylic acid, wherein this 2-hydroxynaphthalene-3-carboxylic acid is obtained in simple manner in the form of a pure compound from the carboxylation melt formed by reaction of the sodium salt of 2-hydroxynaphthalene with carbon dioxide, starting from that melt diluted with water and dissolved, by separating the alkali-soluble acid resins during the work-up of the carboxylation product by means of a cationic surface-active compound containing a quaternary nitrogen atom.

When working up the aqueous solution of the carboxylation melt, the cationic surface-active compound used in accordance with the invention may be added before that step in which the 2-hydroxynaphthalene-3-carboxylic acid is subjected to acidic precipitation, or especially advantageously after neutralization of the alkaline carboxylation melt dissolved in water (by "neutralization", there is to be understood in this case not only adjustment of the pH to about 7, but also adjustment to a weakly acidic range of up to 3.5).

Surprisingly, the cationic surface-active compound used in accordance with the invention forms water-insoluble precipitates with the highly acidic resins, which precipitates are solid or liquid, depending on the choice or precipitation temperature and composition of the surface-active compound. No explanation can be given so far with respect to the nature of these water-insoluble precipitates, which may be salts of these cationic surface-active compounds and the acidic resins linked to each other, or other kinds of bonds, for example aggregates or molecular bonds.

Cationic surface-active compounds to be used in accordance with the invention are the quaternary ammonium compounds of the formula (1)

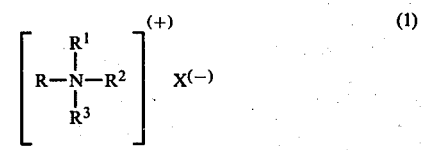

in which R, $R^1$, $R^2$ and $R^3$ may be identical or different from each other and each is an aliphatic redical, an aralkyl or aryl radical, the sum of carbon atoms contained in the substituents R through $R^3$ being at least 8; two or three of the aliphatic radicals, together with the nitrogen atom, may form a heterocyclic ring possibly containing double bonds to which a benzene nucleus may be fused, for example a pyridine, morpholine, imidazoline, benzimidazoline, imidazole, benzimidazole or oxazole ring. The radical $X^{(-)}$ represents the equivalent of an inorganic or organic acid.

By "aliphatic radical" for the symbols R through $R^3$, there are to be understood generally aliphatic straight-chain or branched hydrocarbon radicals having from 1 to 30 carbon atoms which may contain one or more, for example from 1 to 3, double bonds and/or one or more, for example from 1 to 3, hetero-atoms, such as groups of the formulae -O-, -S-, -NH-, or substituted amino groups, or quaternized nitrogen atoms, and/or other groups, for example carboxylic acid amide groups, bound in the aliphatic chain, and/or the aliphatic radicals may be linked to the quaternary nitrogen atom via an oxygen atom. These aliphatic radicals R through $R^3$ may furthermore contain nonionic substituents such as hydroxy, alkyloxy or polyglycol ether groups, these groups consisting preferably of from 1 to 30 carbon atoms. Furthermore, by "aliphatic radicals" there are to be understood hydroaromatic carbocyclic and cycloaliphatic radicals having each from 4 to 8 carbon atoms in the ring; these cyclic radicals optionally carrying aliphatic side chains having from 1 to 12 carbon atoms, or halogen atoms, such as chlorine.

Aralkyl radicals R through $R^3$ are preferably aliphatic radicals having from 1 to 30, preferably 1 to 12, carbon atoms, unsubstituted or substituted by naphthyl and/or phenyl radicals, these aryl radicals optionally containing further substituents such as hydroxy, lower alkyl, lower alkoxy groups and/or halogen atoms, such as chlorine. Aralkyl radicals are for example benzyl, phenylnonyl or phenyldodecyl radicals. Aryl radicals are aromatic carbocyclic radicals, preferably phenyl and naphthyl radicals, unsubstituted or substituted by hydroxy, lower alkoxy, lower alkyl, halogen such as chlorine, carbonamide and/or sulfonamide.

The anion $X^{(-)}$ is for example that of a hydrohalic acid such as the chloride or bromide anion, or that of another inorganic acid, for example the sulfate or hydrogenosulfate anion, an anion of phosphoric or boric acid, an anion of an organic carboxylic acid such as the anion of acetic, formic, oxalic, lactic, tartric, gluconic, citric or benzoic acid, or a radical of an organic sulfonic acid such as the anion of methanesulfonic or benzenesulfonic acid.

Preferred are compounds of the formula (1), in which R is an alkyl of from 8 to 20 carbon atoms, $R^1$ is an alkyl of from 1 to 20 carbon atoms or a di- to hexaethyleneglycol ether radical, or a hydroxyalkyl of from 2 to 6 carbon atoms, or a phenylalkyl of from 4 to 12 carbon atoms in the alkyl moiety, $R^2$ is an alkyl of from 1 to 8 carbon atoms or a hydroxyalkyl of from 2 to 6 carbon atoms, and $R^3$ is an alkyl of from 1 to 8 carbon atoms or a benzyl group.

Quaternary ammonium compounds of the formula (1) to be used in accordance with the invention are for example:

Dodecyl-dimethyl-benzyl-ammonium chloride, Oleyl-trimethyl-ammonium chloride, distearyl-dimethyl-ammonium chloride, lauryl-dimethyl-hydroxyethyl-ammonium chloride, dodecyl-di-(hydroxyethyl)-methyl-ammonium chloride, dodecyl-dimethyl-vinyl-ammonium chloride, dodecyl-methylmorpholinium chloride, lauryl-pyridinium chloride, hexadecyl-N,N'-dimethyl-benzimidazolinium sulfate, dodecyldi-(triethylene-glycol ether)-benzyl-ammonium chloride, phenylnonyl-dimethyl-benzyl-ammonium chloride, oleyl-di-(hydroxyethyl)-ethylene-glycol ether-ammonium chloride, oleyl-dimethyl-hydroxyethyl-ammonium chloride, coconut-di-(triethylene glycol ether)-benzyl-ammonium chloride, coconut-dimethyl-benzyl-ammonium chloride, distearyl-dimethyl-ammonium chloride, trioctyl-methyl-ammonium chloride, coconut-dimethyl-hydroxypropyl-ammonium chloride, p-(isobutyl)-phenoxyethoxyethyl-dimethyl-benzyl-ammonium chloride, oleyl-methyl-imidazolinium chloride, hexadecyl-N,N'-dimethyl-benzimidazolium sulfate, oleyl-methyl-imidazolium chloride, dehydro-abietyl-dimethyl-benzyl-ammonium chloride, preferably for example dodecyl-dimethyl-ammonium chloride, stearyl-dimethyl-benzyl-ammonium chloride, coconut-dimethyl-2,4-dichloro-benzyl-ammonium chloride, trioctyl-methyl-ammonium chloride, cetyl-pyridinium chloride, tetrabutyl-ammonium hydrogeno-sulfate, ($C_{12}$-$C_{16}$-alkyl)-dimethyl-benzyl-ammonium chloride, especially, however, coconut-benzyl-dimethyl-ammonium chloride and benzyl-trimethyl-ammonium chloride.

(By "coconut" there is to be understood a group from a mixture of alkyl, alkenyl and alk-dienyl groups each having from 8 to 18 carbon atoms).

A special embodiment of the work-up process for the carboxylation melt is the following: the carboxylation mixture is diluted with water or dissolved therein at a temperature of at least 80° C., this solution is neutralized with an aqueous mineral acid, preferably hydrochloric or sulfuric acid and preferably adjusted to a pH of from 3.5 to 6.8, preferably 4 to 6.5; insoluble substances are removed from the solution, for example by filtration, the cleared solution (filtrate) is cooled to a temperature of from about 10° to 30° C., preferably 15° to 25° C., the precipitated 2-hydroxynaphthalene is separated, the filtrate thereof is adjusted to a pH of from 0.5 to 2.5, preferably 1 to 2, by means of an aqueous mineral acid, preferably hydrochloric or sulfuric acid, and the precipitated 2-hydroxynaphthalene-3-carboxylic acid is isolated. In this process variant the cationic surface-active compound to be used according to the invention is added after separation of the precipitated 2-hydroxynaphthalene and before adjustment of the pH to 0.5 to 2.5, and the precipitated resin is removed; preferably in this process variant, the cationic surface-active compound is added directly after neutralization of the carboxylation melt which had been dissolved in water, and the precipitated resin is removed.

The first process variant, that is, addition of the cationic surface-active compound before acidic precipitation of the 2-hydroxynaphthalene-3-carboxylic acid requires a further step for separating the precipitate of the resin obtained by means of the compound used in accordance with the invention. This separation is carried out, depending on the kind of cationic surface-active compound, for example by means of a separator or a filter press.

The second process variant, as compared to the one cited first, has the advantage of allowing a simultaneous removal of the resin precipitate obtained by means of the surface-active compound and of the alkali-insoluble resin in one single step, that is, on filtration of the solution of the carboxylation melt adjusted to neutral, especially a pH of from 3.5 to 6.8, by means of an aqueous mineral acid. This second, preferred alternative, wherein the alkali-soluble, acidic resin is precipitated and removed together with the alkali-insoluble resin does not require an additional separation step, so that the usual work-up process for industrial carboxylation mixtures can be maintained without alteration.

The process for the obtention of a pure 2-hydroxynaphthalene-3-carboxylic acid from the reaction mixture of sodium salt of 2-hydroxynaphthalene with carbon dioxide is therefore carried out in a most advantageous manner as follows: the carboxylation melt diluted with water at a temperature of at least 80° C. and dissolved therein is neutralized with an aqueous mineral acid, adjusted to a pH of preferably from 4 to 6.5, the cationic surface-active compound is added, the insoluble substances are removed from the solution, the clarified solution is cooled to a temperature of from 10° to 30° C. the precipitated 2-hydroxynaphthalene is separated, the filtrate is adjusted to a pH of from 0.5 to 2.5 by means of aqueous mineral acid, and the precipitated 2-hydroxynaphthalene-3-carboxylic acid is isolated.

The alkali-soluble acidic resins are precipitated by means of the cationic surface-active compounds from the carboxylation melt on addition of the surface-active compound to the aqueous "neutralized" carboxylation solution. Generally, the cationic surface-active compounds are used in an amount of from 0.1 to 5.0, preferably 0.5 to 3.0% by weight, each relative to the 2-hydroxy-naphthalene-3-carboxylic acid contained in the solution. Precipitation of the alkali-soluble resins by the cationic surface-active compounds in accordance with the invention is quantitative.

It was surprising to observe that the cationic surface-active compounds used in accordance with the invention allow removal of the alkali-soluble acidic resins from the carboxylation melt by precipitation from the aqueous solutions. For, it is the teaching of German Auslegeschrift No. 1,643,541, that cationic surface-active compounds which correspond to formula (1) of the instant invention are used to maintain in solution impurities contained in mixtures of carboxylation products of phenolate carboxylation operations ater mixing with water and subsequent acidification, in order to precipitate the intended hydroxybenzoic acid, and to prevent simultaneous precipitation of these impurities and of the intended hydroxybenzoic acid. It was therefore not to be expected that the cationic surface-active compounds in accordance with this invention can be used for separating the alkali-soluble resins.

The 2-hydroxynaphthalene-3-carboxylic acid obtainable according to the process of the invention is of extraordinary quality and purity; it can therefore be processed without difficulty to pure products such as mentioned above, which for their part, being pure compounds, too, serve for the manufacture of valuable color pigments, or as coupling components for the preparation of pure dyeings according to ice-color dyeing.

The following Examples illustrate the invention; percentages being by weight unless otherwise stated.

EXAMPLE 1

2500 ml of an aqueous solution of a carboxylation melt stemming from a carboxylation reaction of sodium salt of 2-hydroxynaphthalene with carbon dioxide, and containing per liter of solution for example 40 g of 2-hydroxy-naphthalene-3-carboxylic acid is adjusted at 80° C. to a pH of 6.0 by means of a 30% aqueous hydrochloric acid. The alkali-insoluble resin is allowed to sediment within 5 minutes, and then filtered off. The reddish-brown filtrate is cooled to a temperature of 20° C., and the precipitated 2-hydroxynaphthalene is filtered off. This filtrate is heated to 60° C. A pH of 5.0 is adjusted by means of 78% aqueous sulfuric acid. 1 g of coconut-benzyl-dimethyl-ammonium chloride is added, and the solution is stirred at 60° C. for 5 minutes. Subsequently, the precipitated resin is allowed to sediment within 5 minutes, it is then filtered off, the clear solution is heated to 80° C., and a pH of 2.0 is adjusted by means of 78% aqueous sulfuric acid. The precipitated 2-hydroxynaphthalene-3-carboxylic acid is suction-filtered at 80° C. and dried at this temperature until the weight remains constant. 98.5 g of a high-purity 2-hydroxynaphthalene-3-carboxylic acid are obtained.

EXAMPLE 2

Operations for work-up of a carboxylation melt and for separation of the alkali-soluble resins thereof are as described in Example 1. However, instead of the cationic surface-active agent used there, the same amount of another cationic surface-active agent in accordance with the invention is used, for example dodecyl-dimethyl-ammonium chloride, stearyl-dimethyl-benzyl-ammonium chloride, coconut-dimethyl-2,4-dichloro-benzyl-ammonium chloride, benzyl-trimethyl-ammonium chloride, trioctyl-methyl-ammonium chloride or cetyl-pyridinium chloride, or tetrabutyl-ammonium hydrogen sulfate.

The 2-hydroxynaphthalene-3-carboxylic acid is obtained in the same manner as in Example 1, and with the same high yield and purity.

EXAMPLE 3

2500 ml of the solution of the carboxylation melt containing 40 g of 2-hydroxynaphthalene-3-carboxylic acid per liter, as described in Example 1, are adjusted at 80° C. to a pH of 6.0 by means of a 30% aqueous hydrochloric acid. Subsequently, 3 g of coconut-benzyl-dimethyl-ammonium chloride in the form of a 50% aqueous solution are added, the batch is stirred for 5 minutes at 80° C., allowed to sediment for 5 minutes, and the precipitated resin is filtered off together with the alkali-insoluble resin. The light-colored filtrate is then cooled to a temperature of 20° C., and the precipitated 2-hydroxynaphthalene is filtered off. The filtrate is then heated to 80° C., and adjusted to a pH of 2.0 by means of a 78% aqueous sulfuric acid. The then precipitated 2-hydroxynaphthalene-3-carboxylic acid is suction-filtered at a temperature of 80° C., and dried at this temperature until the weight remains constant. It is obtained with a yield of 98.0 g and high purity, corresponding to that of the 2-hydroxynaphthalene-3-carboxylic acid of Example 1.

EXAMPLE 4

2500 ml of a carboxylation melt dissolved in water and containing 60 g of 2-hydroxynaphthalene-3-carboxylic acid per liter are adjusted to a pH of 6.0 at 80° C. by means of an aqueous 30% hydrochloric acid. 6.5 g of coconut-benzyl-dimethyl-ammonium chloride are added, the solution is stirred for 5 minutes at 80° C., allowed to sediment for 5 minutes, and the resin is filtered off. The clear solution obtained is cooled to 20° C., the precipitated 2-hydroxynaphthalene is filtered off. The further work-up of the filtrate is as described in Example 1. 147.6 g of a high-purity 2-hydroxynaphthalene-3-carboxylic acid are obtained.

EXAMPLE 5

2500 ml of a starting solution of the carboxylation melt according to Example 1 are adjusted at 80° C. to a pH of 4.5 by means of 78% aqueous sulfuric acid. 0.5 g of benzyl-trimethyl-ammonium chloride is added, the batch is stirred for 5 minutes at 80° C., allowed to sediment for 5 minutes, and the resin is then filtered off. Subsequently, the filtrate is cooled to 20° C., and the precipitated 2-hydroxynaphthalene is filtered off. The further work-up is as indicated in Example 1. The 2-hydroxy-naphthalene-3-carboxylic acid is obtained with high purity and a yield of 98.2 g.

EXAMPLE 6

2500 ml of the starting solution of the carboxylation melt as indicated in Example 1 are adjusted to pH 6.0 at 80° C. by means of a 30% aqueous hydrochloric acid. The solution is filtered at 80° C. and cooled to 20° C. subsequently. The precipitated 2-hydroxynaphthalene is filtered off, the filtrate is combined at 20° C. with 4.0 g of coconut-benzyl-dimethyl-ammonium chloride. Stirring is continued for 15 minutes at this temperature, the precipitated resin is filtered off, the clear solution is heated to 80° C., and the further work-up is as indicated in Example 1. The high-purity 2-hydroxynaphthalene-3-carboxylic acid is obtained with a yield of 98.3 g.

EXAMPLE 7

Operations for the work-up of a carboxylation melt of sodium salt of 2-hydroxynaphthalene with carbon dioxide and for precipitation of the alkali-soluble resin are as indicated in Example 1. However, instead of the coconut-benzyl-dimethyl-ammonium chloride used there as cationic surface-active agent, the same amount of another cationic surface-active agent in accordance with the invention is used, for example ($C_{12}$-$C_{16}$-alkyl)-dimethyl-benzyl-ammonium chloride, coconut-dimethyl-2,4-di-chlorobenzyl-ammonium chloride, benzyl-trimethyl-ammonium chloride, trioctyl-methyl-ammonium chloride, or tetrabutyl-ammonium hydrogenosulfate.

The 2-hydroxynaphthalene-3-carboxylic acid is obtained in the same manner as in Example 6, and with the same high purity and a yield of 98.0 to 98.5 g.

We claim:

1. In a process for the separation and isolating of 2-hydroxynaphthalene-3-carboxylic acid from the reaction product of the sodium salt of 2-hydroxynaphthalene and carbon dioxide, which comprises
   (a) diluting the resulting carboxylation melt with water and dissolving it,
   (b) adjusting the pH of the solution to a value of about 3.5 to 7 and separating undissolved or precipitated products, and
   (c) recovering and separating 2-hydroxynapthalene-3-carboxylic acid by acidic precipitation and isolating it, the improvement comprises precipitating the alkali-soluble acid resins from the solution of the carboxylation melt by means of a cationic compound added to the solution between steps (b) and (c), said compound corresponding to the formula

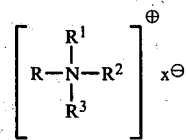

in which R, $R^1$, $R^2$ and $R^3$ are identical or different from each other and each is an unsubstituted or substituted aliphatic radical, an aralkyl or aryl radical, or two or three of the aliphatic radicals form together with the nitrogen atom a heterocyclic ring selected from the group of pyridine, morpholine, imidazoline, benzimidazoline, imidazole, benzimidazole and oxazole, with the proviso that the sum of the carbon atoms of the substituents R through $R^3$ are at least 8, and in which $x^\ominus$ is the equivalent of an inorganic or organic acid.

2. The process according to claim 1 wherein in the cationic surface-active compound of formula (1) R is an alkyl of from 8 to 20 carbon atoms, $R^1$ is an alkyl of from 1 to 20 carbon atoms or a di- to hexa-ethyeleneglycol ether radical, or a hydroxyalkyl of from 2 to 6 carbon atoms, or a phenylalkyl of from 4 to 12 carbon atoms in the alkyl moiety, $R^2$ is an alkyl of from 1 to 8 carbon atoms or a hydroxyalkyl of from 2 to 6 carbon atoms, and $R^3$ is an alkyl of from 1 to 8 carbon atoms or a benzyl group.

3. The process according to claim 1, wherein the cationic surface-active compound used is coconut-benzyl-dimethyl-ammonium chloride.

4. The process according to claim 1, 2 or 3, wherein the cationic surface-active compound is used in an amount of from 0.1 to 5% by weight, relative to 2-hydroxynaphthalene-3-carboxylic acid contained in the carboxylation mixture.

5. The process as claimed in claim 1, 2 or 3, wherein the cationic surface-active compound is used in an amount of from 0.5 to 3% by weight, relative to 2-hydroxynaphthalene-3-carboxylic acid contained in the carboxylation mixture.

* * * * *